United States Patent
Ishiguro et al.

(10) Patent No.: US 9,693,735 B2
(45) Date of Patent: Jul. 4, 2017

(54) BIOLOGICAL SIGNAL AVERAGING PROCESSING DEVICE

(71) Applicant: NIHON KOHDEN CORPORATION, Shinjuku-ku, Tokyo (JP)

(72) Inventors: Takuya Ishiguro, Tokyo (JP); Masahiro Yade, Tokyo (JP); Haruo Fujimoto, Tokyo (JP); Kyosuke Kobayashi, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 741 days.

(21) Appl. No.: 14/140,056

(22) Filed: Dec. 24, 2013

(65) Prior Publication Data

US 2014/0195202 A1    Jul. 10, 2014

(30) Foreign Application Priority Data

Jan. 8, 2013   (JP) ................................ 2013-001177

(51) Int. Cl.
  *G06F 15/00*   (2006.01)
  *H03F 1/26*    (2006.01)
  (Continued)

(52) U.S. Cl.
  CPC ........ *A61B 5/7235* (2013.01); *A61B 5/04012* (2013.01); *A61B 5/0476* (2013.01); *A61B 5/0484* (2013.01); *A61B 5/7203* (2013.01)

(58) Field of Classification Search
  CPC ........... G06F 3/04842; G06F 17/30958; G06F 17/30528; G06F 17/30551;
  (Continued)

(56) References Cited

U.S. PATENT DOCUMENTS

2004/0106870 A1* 6/2004 Mast ........................ A61B 8/08
                                                     600/443
2004/0254443 A1   12/2004 Gott et al.
(Continued)

FOREIGN PATENT DOCUMENTS

CN    102697495 A    10/2012
JP    5-203491 A      8/1993
(Continued)

OTHER PUBLICATIONS

Communication from the European Patent Office issued Jan. 14, 2016 in a counterpart European Application No. 13198513.7.
(Continued)

*Primary Examiner* — Roy Y Yi
(74) *Attorney, Agent, or Firm* — Sughrue Mion, PLLC (57) ABSTRACT

The biological signal averaging processing device includes a waveform input unit for continuously obtaining a biological signal in which analogous waves appear repeatedly, a summing-averaging processing unit which sums the biological signal obtained from the waveform input unit each time a predetermined time period lapses after a desired start time point to obtain an average wave, a noise level detection part which detects a noise level of random noise contained in the biological signal obtained from the waveform input unit each time the predetermined time period lapses after the desired start time point, a display part for displaying information, and a display control part for displaying the information on the screen of the display part. The display control part displays the noise levels detected by the noise level detection part on the screen of the display part in a chronological manner in association with the respective predetermined time periods.

6 Claims, 8 Drawing Sheets (51) Int. Cl.
    *H04B 15/00*     (2006.01)
    *A61B 5/00*     (2006.01)
    *A61B 5/0476*     (2006.01)
    *A61B 5/0484*     (2006.01)
    *A61B 5/04*     (2006.01)

(58) Field of Classification Search
    CPC ........... G06F 17/30554; G06F 19/3418; G06F 3/0482; G06F 17/2247; G06F 17/246; G06F 17/30; G06F 17/30424; G06F 2203/04808; G06F 3/048; A61B 3/0025; A61B 8/5207; A61B 3/0041; A61B 3/113; A61B 5/0022; A61B 5/14532; A61B 8/14; A61B 2503/10; A61B 2560/0238; A61B 3/102; A61B 5/0017; A61B 5/01; A61B 5/1114; A61B 5/1124
    See application file for complete search history.

(56) References Cited

U.S. PATENT DOCUMENTS

| | | |
|---|---|---|
| 2009/0228399 A1 | 9/2009 | Connors et al. |
| 2011/0196615 A1* | 8/2011 | Vitali .................. G06K 9/0053 702/19 |

FOREIGN PATENT DOCUMENTS

| | | |
|---|---|---|
| JP | 8-171415 A | 7/1996 |
| JP | 11-123181 A | 5/1999 |
| JP | 2002-224068 A | 8/2002 |
| JP | 2005-296407 A | 10/2005 |
| WO | 00/21438 A1 | 4/2000 |
| WO | 02/062217 A1 | 8/2002 |

OTHER PUBLICATIONS

Communication issued Apr. 25, 2016, issued by the State Intellectual Property Office of the People's Republic of China in counterpart Chinese Patent Application No. 201310727452.5.
Communication dated Apr. 18, 2016 issued by Japanese Intellectual Property Office in counterpart Japanese Application No. 2013-001177.
Office Action dated Apr. 1, 2015, issued by the European Patent Office in counterpart European Application No. 13198513.7.
Extended European Search Report, dated Mar. 13, 2014, issued by the European Patent Office in counterpart European Application No. 13198513.7.
"Basic Knowledge and Safety Management of ME"; Revised Fifth Edition; Japanese Society for Medical and Biological Engineering; Nankodo Co., Ltd.; Dec. 10, 2008; pp. 1-6.
Communication dated Oct. 25, 2016 issued by the European Patent Office in counterpart European Patent Application No. 13198513.7.

* cited by examiner

3.6455μ V (1 MINUTE)

2.4741μ V (2 MINUTES)

1.4239μ V (3 MINUTES)

*0.9761μ V (4 MINUTES)*

*0.8166μ V (5 MINUTES)*

*0.7996μ V (6 MINUTES)*

*0.5996μ V (7 MINUTES)*

0.2996μ V (8 MINUTES)

0.2966μ V (9 MINUTES)

BIOLOGICAL SIGNAL AVERAGING PROCESSING DEVICE

BACKGROUND

The presently disclosed subject matter relates to a biological signal averaging processing device which subjects a biological signal formed by repeatedly appearing analogous waves to a summing-averaging processing to thereby remove random noise therefrom. In the present specification, noise means a signal other than a required biological signal and includes an unnecessary biological signal as well as disturbance noise.

A signal-averaged electrocardiogram test may be performed in order to predict cardiac sudden death. A patient, who likely dies suddenly due to cardiac cause, is apt to generate a delayed minute potential (late ventricular potential (LP: late potential)) at the end portion of a QRS wave in an electrocardiogram. Conventionally, the signal-averaged electrocardiogram test has been performed in order to detect the LP. JP-A-2002-224068 discloses a method of detecting the LP. According to this literature, an XYZ lead electrocardiogram led from electrodes connected to a patient's body is converted into time-series digital data, and then subjected to the summing-averaging processing in synchronism with R-wave positions to thereby detect the LP.

The summing-averaging processing is performed in order to detect a minute LP accurately by removing the influence of noise (random noise).

A non-patent document 1 discloses a cerebral evoked potentiometer which detects, mainly from the scalp, changes of minute potentials led to respective sensory areas of a cerebrum in response to a stimulation to visual sense, auditory sense and somatic sense etc., in order to detect various kinds of abnormalities of a central nervous system due to cerebral tumor, cerebral infarction etc., and functional abnormality of sensory pathways to the respective sensory areas of the cerebrum via a brain stem from various kinds of sensory receptors of periphery, for example.

The minute potentials thus led contain a visual evoked potential (VEP) led by a stimulation of flash and pattern light, a somatosensory evoked potential (SEP) obtained by electrically stimulating a sensory nerve of periphery, a long-latency auditory evoked potential (AEP) led by a stimulation of tone burst or click and an auditory brainstem response (ABR) etc. These potentials are minute potentials almost in a range from 0.1 to 10 µV buried within an electroencephalographic signal.

The electroencephalographic signal containing the evoked potentials is subjected to an analog-to-digital conversion and subjected to the summing-averaging processing in synchronism with stimulations, whereby the evoked potentials buried within noise, that is, electroencephalogram can be detected. As potentials for obtaining a required biological signal by removing the random noise through the summing-averaging processing, there are the somatosensory evoked potential (SEP), a brainstem auditory evoked potential (BAEP), the visual evoked potential (VEP) and various kinds of event related potentials (ERP), for example.

PRIOR ART LITERATURE

[Non-Patent Literature 1] "Basic Knowledge and Safety Management of ME, revised fifth edition", supervised by (Incorporated Association) Japanese Society for Medical and Biological Engineering, published by Nankodo Co., Ltd, Dec. 10, 2008, pp. 150 to 153

In the related art, the signal-averaged electrocardiogram test per one time is tried to be finished about 10 minutes at the maximum in view of bearing of a person to be tested. However, there sometimes arises a case that the test can not be finished 10 minutes since the reduction degree of noise level is difficult to grasp.

Each of the potentials such as the somatosensory evoked potential (SEP), the brainstem auditory evoked potential (BAEP), the visual evoked potential (VEP) and the various kinds of event related potentials (ERP) is required to be repeatedly summed in order to remove random noise such as electroencephalogram to thereby obtain required wave. However, since the summation is performed after determining the number of summation in advance, there arises a problem that the summation is likely excessive or deficient and hence the processing can not be performed efficiently.

SUMMARY

This presently disclosed subject matter provides a biological signal averaging processing device which can display a state that random noise is removed by using a summing-averaging processing, in an easily understood manner.

An aspect of the presently disclosed subject matter provides a biological signal averaging processing device comprising:

a signal acquisition unit configured to continuously obtain a biological signal in which analogous waves appear repeatedly; and a summing-averaging processing unit configured to subject the analogous waves obtained by the signal acquisition unit to a summing-averaging processing to thereby obtain an average wave each time succeeding predetermined time period lapses after a desired start time point or each time a predetermined number of succeeding analogous waves appear after the desired start time point, thereby taking out a biological signal from which random noise contained therein is removed, the biological signal averaging processing device further comprising:

a noise level detection unit configured to detect noise levels of the random noise contained in the biological signal which is obtained by the signal acquisition unit, each time the succeeding predetermined time period lapses after the desired start time point or each time the predetermined number of the succeeding analogous waves appear after the desired start time point;

a display unit configured to display information; and a display control unit configured to display information on a screen of the display unit, wherein the display control unit displays the noise levels detected by the noise level detection unit in a chronological manner in association with the respective succeeding predetermined time periods or the respective predetermined number of the succeeding analogous waves.

The biological signal may be an electroencephalographic signal, the summing-averaging processing unit may subject the electroencephalographic signal obtained by the signal acquisition unit to the summing-averaging processing to obtain a signal-averaged electrocardiogram, each time the succeeding predetermined time period lapses after the desired start time point, and the signal-averaged electrocardiogram, at a time where the noise level of the random noise detected by the noise level detection unit is smaller than a predetermined level, may be used for a signal-averaged electrocardiogram test.

The display control unit may display noise levels on the display unit as at least one of numerical values and graphs each of which are related to the respective succeeding predetermined time periods or the respective predetermined number of the succeeding analogous waves.

The display control unit may change a display mode of noise levels displayed on the screen of the display unit when the noise level exceeds a threshold value.

The display mode may be changed by change of color, change of texture, or at least one of change of thickness, size, font and style of characters.

The biological signal averaging processing device may further comprise:

a noise level prediction unit configured to predict noise levels after a newest noise-level detection time point by using noise levels having been detected by the noise level detection unit, wherein the display control unit displays noise levels predicted by the noise level prediction unit on the screen of the display unit.

The display control unit may display, on the screen of the display unit, the noise levels having been detected until the newest noise-level detection time point in association with the respective succeeding predetermined time periods or the respective predetermined number of the succeeding analogous waves, together with the predicted noise levels.

DETAILED DESCRIPTION OF EMBODIMENTS

Hereinafter, a first embodiment of a biological signal averaging processing device according to the presently disclosed subject matter will be explained with reference to accompanying drawings. In the respective figures, same constitutional elements are referred to by the common symbols, with duplicated explanation thereof being omitted.

Figure 1:
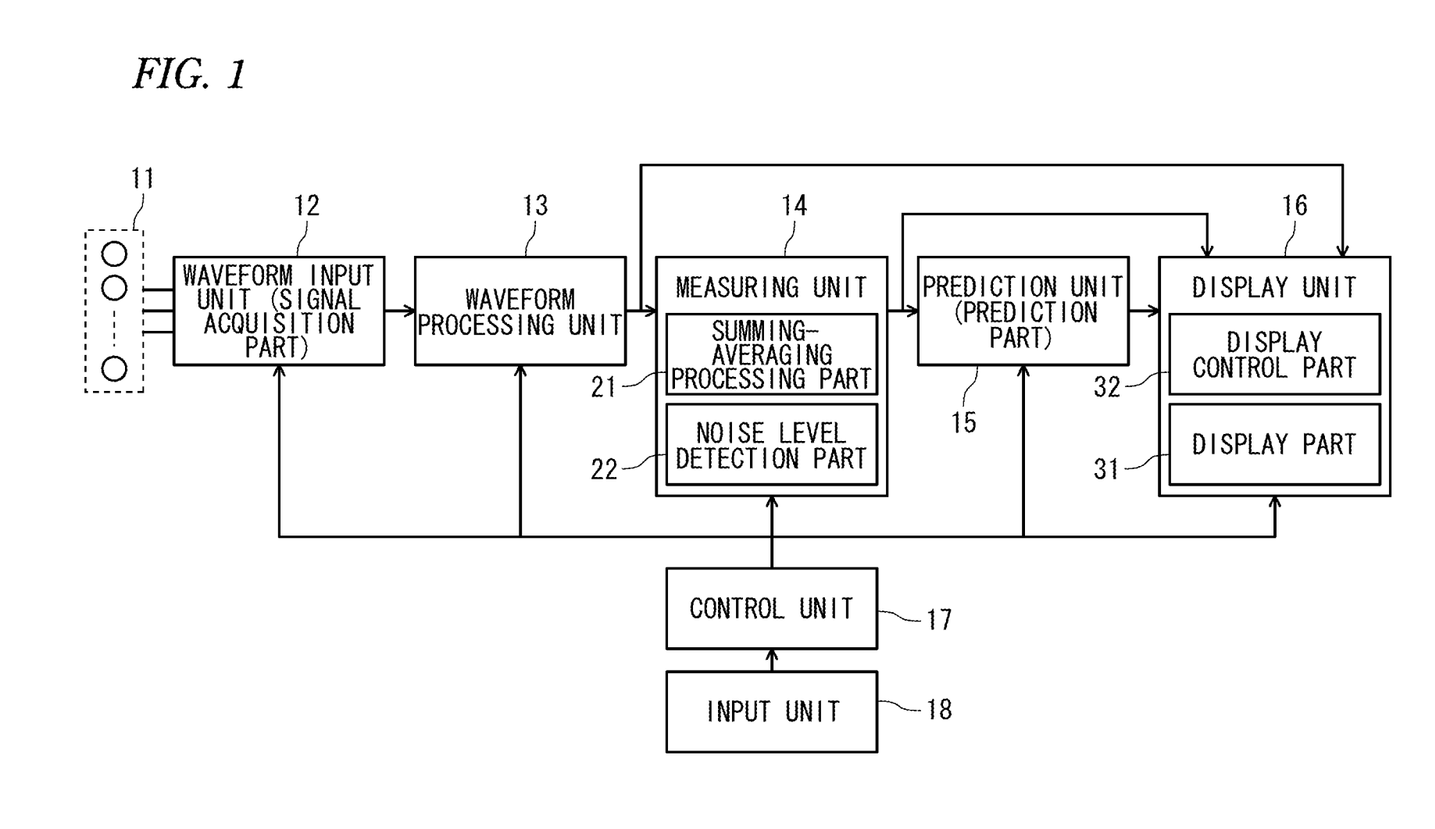
FIG. 1 is a functional block diagram illustrating the first embodiment of a biological signal averaging processing device according to the presently disclosed subject matter.

FIG. 1 is a diagram illustrating the configuration of the embodiment in a case where the biological signal averaging processing device according to the presently disclosed subject matter is applied to a signal-averaged electrocardiogram test device. The signal-averaged electrocardiogram test device may include a waveform input unit 12, a waveform processing unit 13, a measuring unit 14, a prediction unit 15, a display unit 16, a control unit 17 and an input unit 18.

The waveform input unit 12 acts as a signal acquisition part. The waveform input unit 12 is connected to an electrode unit 11 and receives an electrocardiographic signal from the electrode unit 11. The electrocardiographic signal may be an XYZ lead electrocardiographic signal, for example. In this case, the electrode unit 11 is provided with electrodes the number of which is chosen to be enough to obtain the XYZ lead electrocardiographic signal. The waveform input unit 12 subjects the electrocardiographic signal thus taken is to an analog-to-digital conversion to obtain digital waveform data.

The waveform processing unit 13 obtains the waveform data from the waveform input unit 12 and performs a filtering processing as to the waveform data, and further detects a QRS wave. The measuring unit 14 receives the waveform data and the QRS wave detection result etc. from the waveform processing unit 13 and performs a measurement/analysis processing as the signal-averaged electrocardiogram test device in accordance with predetermined algorithm. The measurement/analysis processing contains a processing of obtaining various kinds of parameters such as the LP by using the signal-averaged electrocardiogram obtained from a summing-averaging processing part 21 described later. The signal-averaged electrocardiogram test is performed based on the various kinds of parameters. The measuring unit 14 may include the summing-averaging processing part 21 and a noise level detection part 22.

Figure 2:
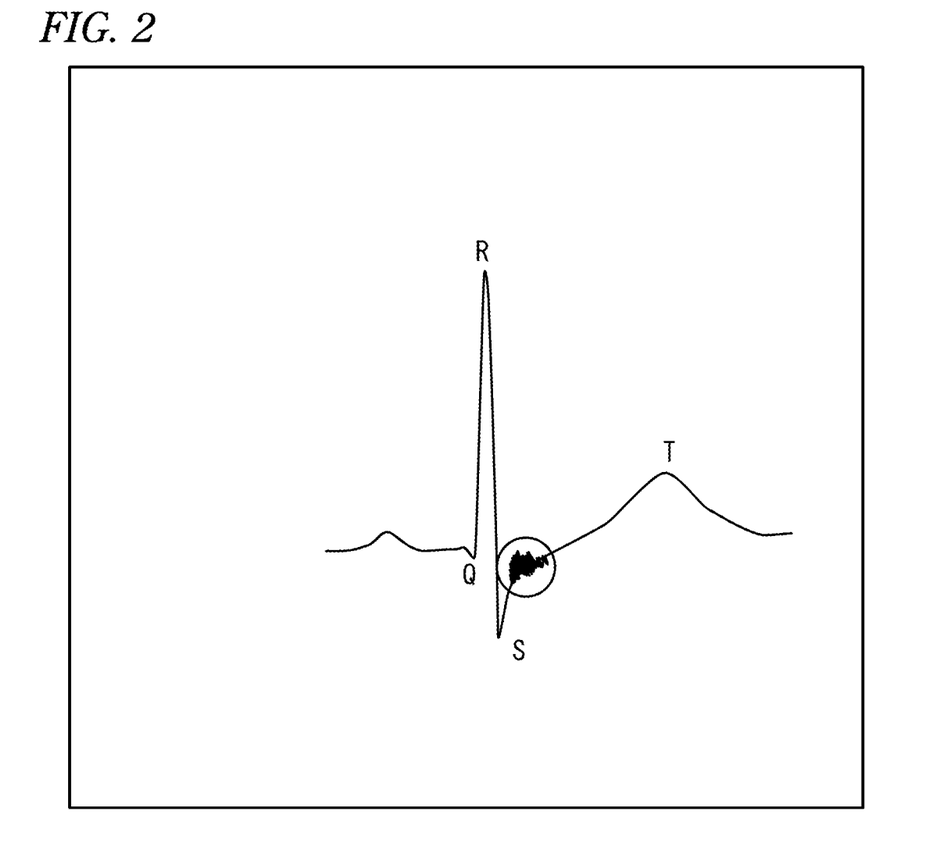
FIG. 2 is a diagram illustrating an electrocardiographic waveform for explaining a signal-averaged electrocardiogram in the first embodiment of the biological signal averaging processing device according to the presently disclosed subject matter.

The summing-averaging processing part 21 sequentially sums the waveform data at every pulse of the electroencephalographic signal and obtains an average thereof to thereby obtain the signal-averaged electrocardiogram, based on the waveform data and the QRS wave detection result from the waveform processing unit 13. To be explained in detail, the waveform data is sequentially summed at every pulse during a predetermined time period (one minute, for example) after the start of the test to thereby obtain a signal-averaged electrocardiogram. Then, the waveform data is sequentially summed at every pulse until the next predetermined time period lapses after the start of the test to thereby obtain another signal-averaged electrocardiogram. Hereinafter, in the similar manner, a signal-averaged electrocardiogram is obtained each time the succeeding predetermined time period lapses after the start of the test. Thus, as shown in FIG. 2, random noise is removed from the final signal-averaged electrocardiogram according to the summing processing. That is, an LP wave (shown within a circle in FIG. 2) appears at the end portion of the QRS wave.

The noise level detection part 22 detects a noise level from the test start time point at every lapse of the succeeding predetermined time period. To be explained in detail, at every pulse within the predetermined time period, wave within a time period (hereinafter called a reference time period) determined with reference to an R wave is taken out to thereby obtain a maximum potential difference of the wave (a potential difference between the highest potential and the lowest potential of the wave). Then, an average value of the maximum potential differences within the predetermined time period is obtained. Thereafter, a standard deviation (SD) of the maximum potential difference is obtained based on differences between the maximum potential differences at respective pulses and the average value of the maximum potential differences. The standard deviation thus obtained is set as a noise level at this time point. The reference time period may contain a time period where the R wave exists, whilst may not contain the time period where the R wave exists but may be a suitable time period before or after the R wave. When a section where a base line appears between a P wave and a Q wave before the P wave is set as an example of the reference time period, favorably only random noise appears at the section.

The aforesaid noise level at this time point can also be obtained by using the signal-averaged electrocardiogram in the predetermined time period. To be concrete, a standard deviation is obtained based on respective potentials of the waves of the signal-averaged electrocardiogram existing within the reference time period and an average value thereof, and this standard deviation is set as the noise level at this time point. Alternatively, a difference between the maximum value and the minimum value of the potential of the waves existing within the reference time period, that is, the maximum potential difference may be set as the noise level at this time point.

The noise levels obtained upon respective lapses of the succeeding predetermine time period are sent to the prediction unit 15 and the display unit 16. The display unit 16 may include a display part 31 for displaying information and a display control part 32. The display part 31 is a display device such as an LCD. The display control part 32 receives the noise levels and displays on the screen of the display part 31 an image in which these noise levels are made associated with the respective lapses of the succeeding predetermine time period. The noise level may be displayed upon every lapse of integral multiple of the succeeding predetermine time period.

The prediction unit 15 is a noise level prediction part which predicts, using the noise levels having been detected by the noise level detection part 22, noise levels after the current time point. The noise levels after the current time point predicted by the prediction unit 15 are sent to the display control part 32 of the display unit 16. The display control part 32 prepares a prediction image based on the predicted noise levels and displays it on the screen of the display part 31. The prediction unit 15 obtains, using the noise levels having been obtained hereinbefore, noise levels being predicted hereinafter, that is, the predicted noise levels in a manner of performing a straight-line approximation or a curve approximation. In this case, the prediction unit 15 analyzes the noise level at the current time point and predicts noise levels newly each time the detected noise level is updated. Incidentally, the prediction unit 15 may be configured in a manner that chronological changes of the noise levels detected in the past are stored in a not-shown storage unit, and the noise levels stored in the storage unit which chronological change is similar to that of a noise level change currently detected are taken out as the predicted noise levels.

The display control part 32 obtains trend waveform data from the waveform processing unit 13, then prepares respective lead electrocardiograms based on the waveform data and displays on the screen of the display part 31. Further, the display control part 32 may be configured to display, on the screen of the display part 31, the result (various kinds of parameters such as LP, for example) of the measurement/analysis performed by the measuring unit 14 as an image.

The input unit 18 may be configured so as to have keys for inputting commands such as the start/stop of the signal-averaged electrocardiogram test, the switching relating to display of the noise level, and the display of measurement/analysis result of the measuring unit 14. The command inputted by the input unit 18 is received by the control unit 17, whilst the control unit 17 sends control information corresponding to the command to the waveform input unit 12, the waveform processing unit 13, the measuring unit 14, the prediction unit 15 and the display unit 16.

The operation of the signal-averaged electrocardiogram test device configured in this manner will be explained. The electrodes of the electrode unit 11 are pasted to predetermined positions of body of a test subject. Then, a power supply is turned on and the start of the signal-averaged electrocardiogram test is inputted, by operating the input unit 18. Thus, the control unit 17 instructs the start of the signal-averaged electrocardiogram test to the respective units. The waveform input unit 12 obtains the electrocardiographic signal from the electrode unit 11 and subjects the electrocardiographic signal to the analog-to-digital conversion to thereby output digital waveform data. The waveform processing unit 13 performs the filtering processing as to the waveform data sent from the waveform input unit 12, and further detects a QRS wave.

Figure 3:
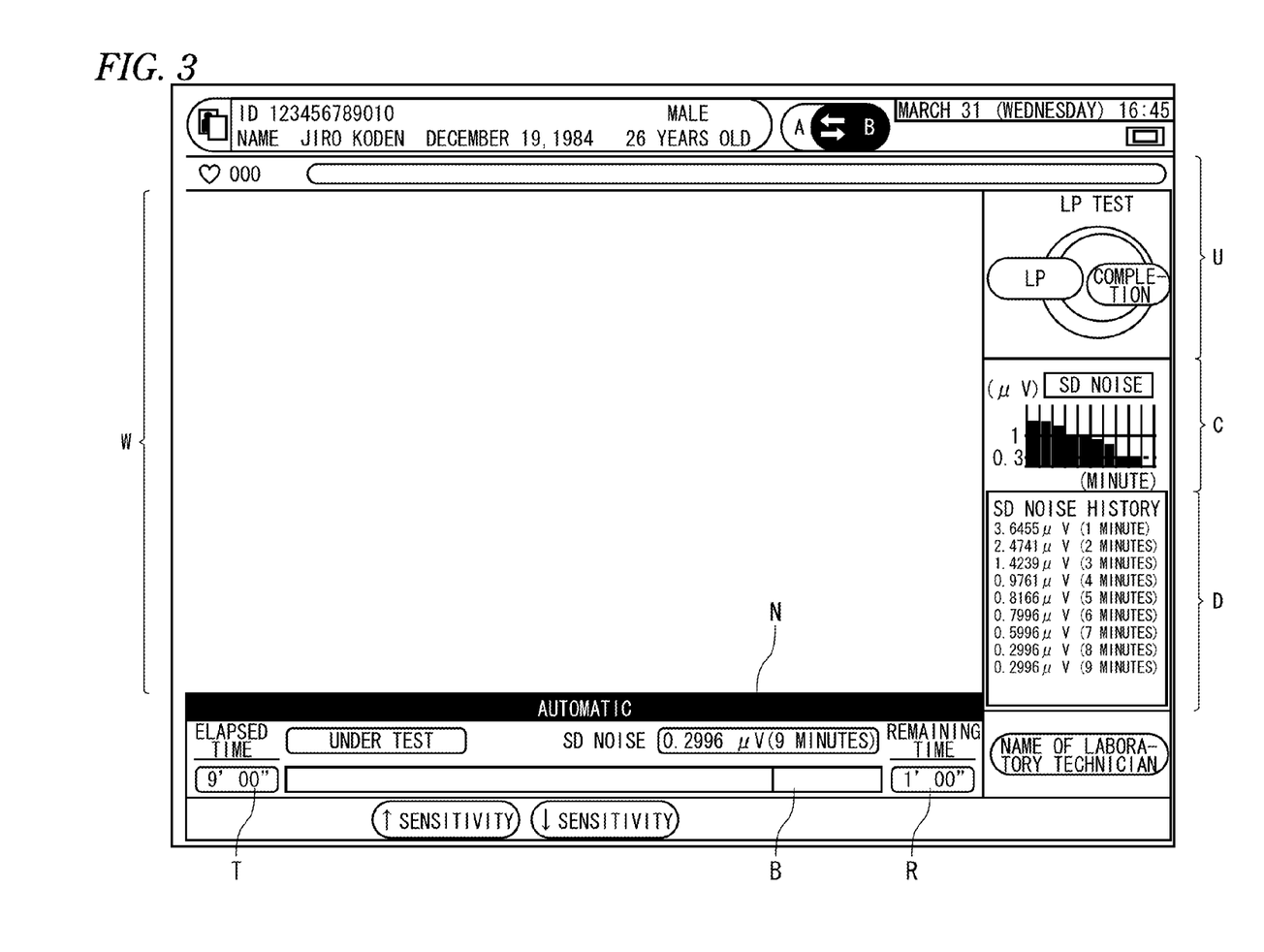
FIG. 3 is a diagram illustrating an example of a display screen relating to an electrocardiogram and noise levels to be displayed in the first embodiment of the biological signal averaging processing device according to the presently disclosed subject matter.

Since the waveform data is sent to the display unit 16, the display control part 32 obtains trend waveform data from the waveform processing unit 13 and prepares respective lead electrocardiograms based on the waveform data to thereby display on a waveform display area W in the screen shown in FIG. 3. The display control part 32 may display the measurement/analysis result etc. of the signal-averaged electrocardiogram test device at a part or entirety of the waveform display area W.

The measuring unit 14 obtains the waveform data and the QRS wave detection result etc. from the waveform processing unit 13 and performs the measurement/analysis processing as the signal-averaged electrocardiogram test device, as described above. That is, the summing-averaging processing part 21 performs a summing-averaging processing and the noise level detection part 22 detects noise levels.

The display control part 32 of the display unit 16 receives the noise levels and prepares an image in which these noise levels are made correspond to the respective lapses of the succeeding predetermine time periods. This image may be at least one of a numerical image and a graphic image in each of which the noise levels are made correspond to the respective lapses of the succeeding predetermine time periods. FIG. 3 shows an example of the screen of the display part 31 that displays, as "SD Noise", both the numerical image and the graphic image in each of which the noise levels are made correspond to the respective lapses of the succeeding predetermine time periods. In this example, the rightmost area among five areas of the screen divided almost equally in the vertical direction is set as a display area relating to the LP.

The lower area of the screen shown in FIG. 3 includes an area N for displaying a current value of the noise level, an area T for displaying the elapsed time, an area R for displaying a remaining time, and an area B for displaying the elapsed time as a bar. The display control part 32 displays images on these areas.

The display control part 32 holds time data (10 minutes, for example) until the completion of a single test and displays, as an image, a progress situation from the start of the test at an upper area U on the upper side of the center area C of the display area relating to the LP in FIG. 3. In this embodiment, an image is displayed in which bold arcs couple between a button drawing "LP" and a button drawing "Complete". To be concrete, the progress situation from the start of the test is displayed in a manner that the bold arcs progress toward the button drawing "Complete". In this manner, the progress situation can be recognized visually.

Further, the graphic image (although a bar graph is shown in the figure, a polygonal line graph etc. may be displayed in place thereof) of noise levels corresponding to the respective lapses of the succeeding predetermine time periods is displayed at the center area C of the display area relating to the LP shown in FIG. 3. In this graphic image, when the noise level exceeds a threshold value, the display mode, that is, color tone of the image corresponding to the exceeded noise level is changed. To be concrete, supposing that the threshold values are 1 µV and 0.3 µV, the color tone may be changed into red when the noise level is larger than 1 µV, the color tone may be changed into yellow when the noise level is equal to or smaller than 1 µV and larger than 0.3 µV, and the color tone may be changed into blue when the noise level is equal to or smaller than 0.3 µV. The lines of the threshold values may also be displayed.

The numerical image of noise levels corresponding to the respective lapses (one minute) of the succeeding predetermine time periods is displayed at a lower area D on the lower side of the center area C of the display area relating to the LP. In this numerical image, also like the graphic image, when the noise level exceeds the threshold value, color tone of the image corresponding to the exceeded noise level is changed. Of course, numerical values themselves may be displayed in place of the numerical image. In this case, the color of the numerical values is changed.

Figure 4:
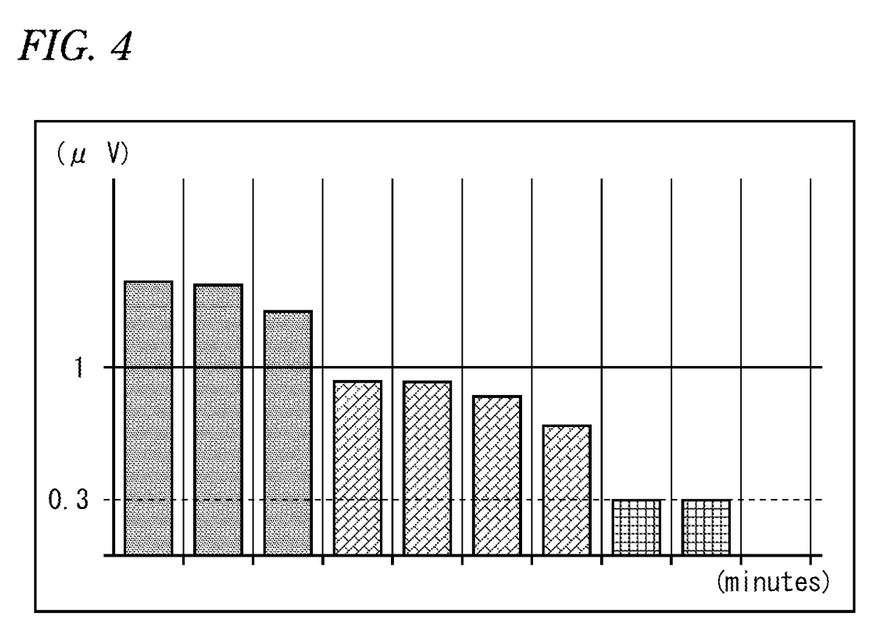
FIG. 4 is a diagram illustrating the second example of the display screen relating to noise levels to be displayed in the first embodiment of the biological signal averaging processing device according to the presently disclosed subject matter.
Figure 5:
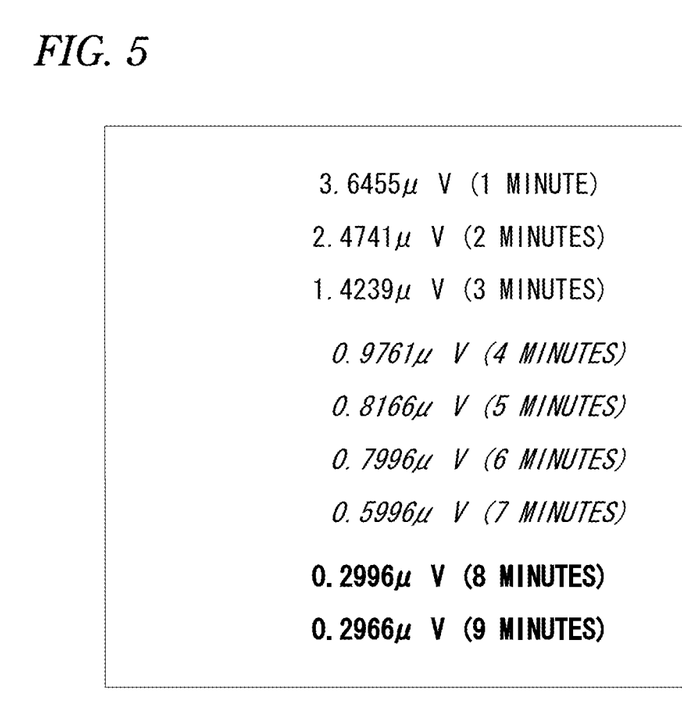
FIG. 5 is a diagram illustrating the third example of the display screen relating to noise levels to be displayed in the first embodiment of the biological signal averaging processing device according to the presently disclosed subject matter.

FIG. 4 illustrates an example where the graphic image displayed at the center area C of the display area relating to the LP is displayed in another display mode. In this graphic image, the texture within the bar graph is changed when the noise level represented by this bar graph exceeds the threshold value. FIG. 5 illustrates an example where the numerical image displayed at the lower area D of the display area relating to the LP is displayed in another display mode. In this numerical image, the thickness, size, font and style of each of the characters corresponding to the exceeded noise level are changed when the noise level exceeds the threshold value. Instead of this, at least one of the thickness, size, font and style of each of the characters may be changed.

Since the images are displayed in the aforesaid manner, when the noise level larger than 1 µV as the threshold value continues for about 4 minutes after the start of the test without scarcely changing it's level, the command for stopping the signal-averaged electrocardiogram test can be inputted from the input unit 18 to thereby stop the operations of the respective units via the control unit 17. Then, after checking the electrodes of the electrode unit 11 etc., the command for starting the signal-averaged electrocardiogram test can be inputted again from the input unit 18 to thereby perform the test. Thus, the test can be performed efficiently without continuing for a long time such the test large in the noise level and low in the reliability.

Figure 6:
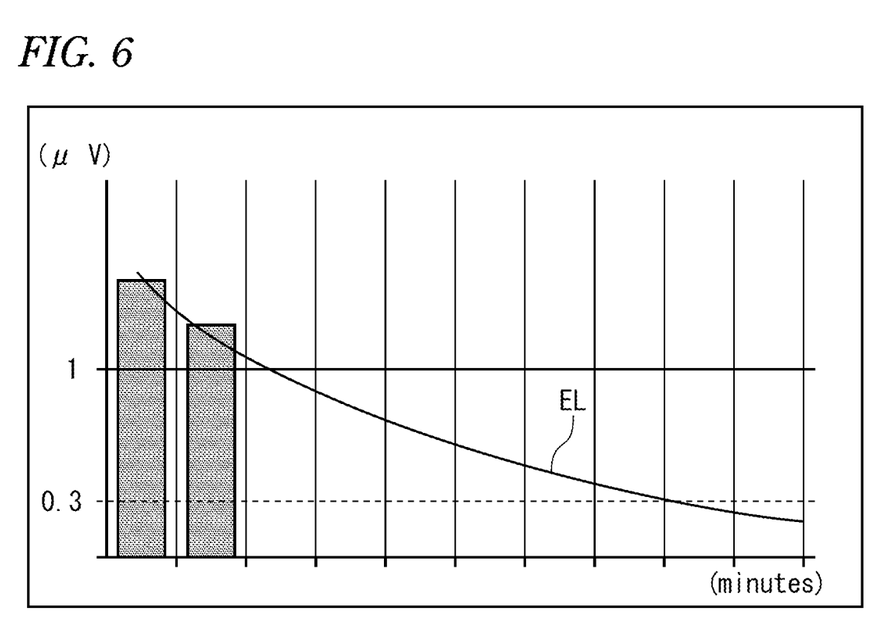
FIG. 6 is a diagram illustrating an example of the display screen relating to predicted noise levels to be displayed in the first embodiment of the biological signal averaging processing device according to the presently disclosed subject matter.
Figure 7:
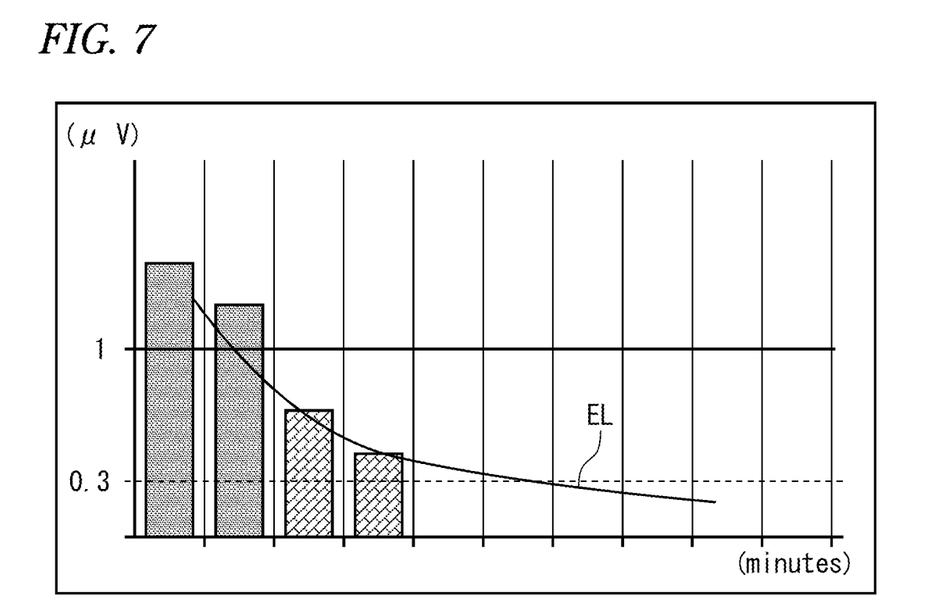
FIG. 7 is a diagram illustrating an example of the display screen relating to predicted noise levels to be displayed, in which the noise level detection has been progressed than FIG. 6, in the first embodiment of the biological signal averaging processing device according to the presently disclosed subject matter.

During the signal-averaged electrocardiogram test, when the command for switching the prediction display of noise level is inputted from the input unit 18, the graphic image to be displayed at the center area C of the display area relating to the LP is displayed as shown in FIG. 6 or 7. FIG. 6 illustrates a case that the noise level has been detected until the lapse of 2 minutes after the start of the test. When the aforesaid command concerning the switching is inputted from the input unit 18, the prediction unit 15 predicts noise levels after this time point by using the noise levels having been detected by the noise level detection part 22. The predicted noise levels are sent to the display control part 32. When the display control part 32 receives a command concerning the switching into the prediction display of noise level from the control unit 17 in corresponding to the command input from the input unit, the display control part prepares a prediction image based on the predicted noise levels.

As shown in FIG. 6, in this predicted image, a curve EL, for example, obtained by approximating the predicted noise levels is drawn as well as the noise levels respectively detected upon the lapses of one minute and two minutes after the start of the test. Since the prediction unit 15 hereinafter predicts noise levels newly each time the detected noise level is updated, the predicted noise levels may also change.

FIG. 7 illustrates an example in a case that the noise level detection has been progressed until the lapse of 4 minutes after the start of the test. As shown in FIG. 7, in this predicted image, a curve EL obtained by approximating the predicted noise levels is drawn as well as the noise levels respectively detected upon the lapses of one minute, two minutes, three minutes and four minutes after the start of the test. As compared with the case of FIG. 6, since the noise level detection has been progressed, the curve EL shown in FIG. 7 represents that the noise level is predicted to reduce earlier than the case of FIG. 6.

Since the images are displayed in the aforesaid manner, when the reduction of noise level can not be expected according to the prediction, the command for stopping the signal-averaged electrocardiogram test can be inputted from the input unit 18 to thereby stop the operations of the respective units via the control unit 17. Thus, the test can be performed efficiently without continuing for a long time such the test large in the noise level and low in the reliability.

Although the explanation is made as to the case where the predicted noise levels are displayed only by the graphic image, the predicted noise levels may be displayed by a numerical image or the combination of a graphic image and a numerical image. The graphic image is not limited to the bar graph or the line graph but may be an image capable of displaying the detected noise levels and the predicted noise levels in a distinguishable manner therebetween. When the predicted noise levels are being displayed, if the command for switching the display of noise level is inputted from the input unit 18, the display can be restored to the display of the detected noise levels. Although this embodiment is arranged in a manner that the command concerning the switching of the display of noise level is inputted from the input unit 18, the predicted noise levels as shown in FIG. 6 or 7 may be displayed initially.

Next, a second embodiment of a biological signal averaging processing device according to the presently disclosed subject matter will be explained. In the aforesaid first embodiment, although the explanation is made as to the case where the presently disclosed subject matter is applied to a signal-averaged electrocardiogram test device, the presently disclosed subject matter can be applied to all devices capable of obtaining a biological signal wave which is required to remove random noise therefrom by performing the summing-averaging processing. As examples of a required biological signal wave, there are the somatosensory evoked potential (SEP), the brainstem auditory evoked potential (BAEP), the visual evoked potential (VEP) and various kinds of event related potentials (ERP), for example. Each of them is a biological signal (potential) which is generated (led) at a predetermined position by stimulating a particular part of a living body, and is used for a test etc. for specifying a lesion by measuring and analyzing the potential.

As an example, the explanation will be made as to a case where the biological signal averaging processing device according to the presently disclosed subject matter is applied to a visual evoked potential (VEP) measuring device. The VEP is a potential led to the visual cortex of a brain when a light stimulation is applied to a retina, and is measured for a function test etc. of optic nerve. The VEP is measured in a manner that a light stimulation is continuously applied to an eye at predetermined timings to thereby detect reaction potentials (reaction waves) by electrodes attached to a head. Since the detected waves contain normal brain waves (α wave, β wave etc.) etc. in addition to the reaction waves, waves detected in response to a single stimulation are continuously subjected to the summing-averaging processing to remove the normal brain waves etc. to thereby extract only the reaction waves (VEP). The normal brain waves etc. correspond to random noise. This embodiment will be explained in detail.

Figure 8:
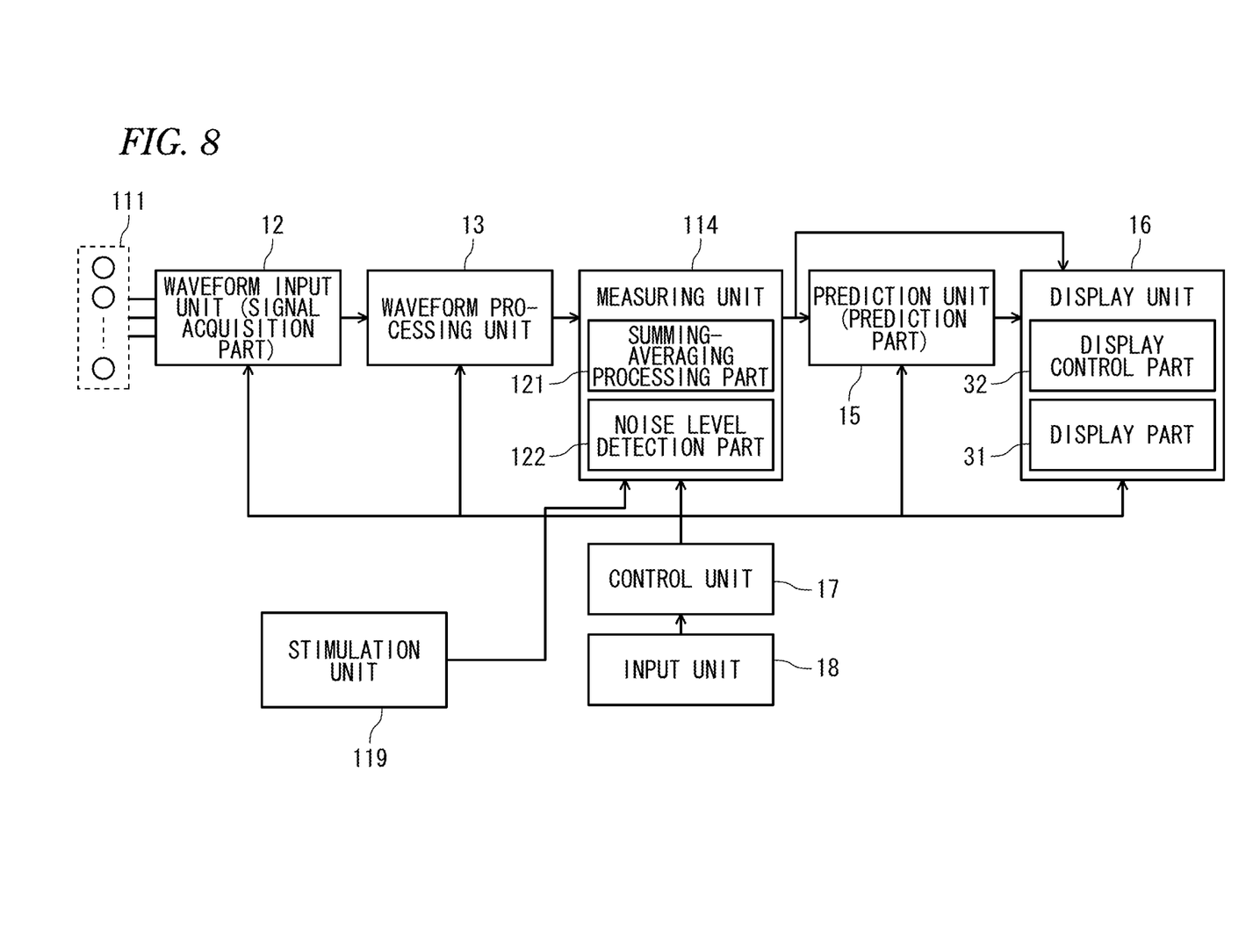
FIG. 8 is a functional block diagram illustrating the second embodiment of a biological signal averaging processing device according to the presently disclosed subject matter.

FIG. 8 is a diagram illustrating the configuration of the visual evoked potential measuring device according to the second embodiment of the presently disclosed subject matter. In FIG. 8, constituent elements identical to those of the first embodiment are referred to by the common symbols, with explanation thereof being omitted. This embodiment largely differs from the first embodiment in that a potential led in response to a stimulation applied from the outside is detected and an interval of the display of a noise level is determined by the number of applied stimulations.

In the visual evoked potential measuring device, a stimulation unit 119 continuously applies stimulations to an eye at the predetermined timings, and an electrode unit 111 attached to a head detects a VEP signal containing random noise such as the normal brain waves etc. at every stimulation (hereinafter a VEP signal containing the random noise is referred to "VEP signal etc." and a VEP signal from which the random noise is removed is referred to "VEP signal"). The number of stimulations is set in accordance with the magnitude etc. of the VEP signal.

A measuring unit 114 receives waveform data such as the VEP signal from a waveform processing unit 13, then, in order to obtain the VEP signal, subjects the VEP signal etc. to a summing-averaging processing at every stimulation and also obtains a noise level at every predetermined number of stimulations from the start of the measurement of the VEP signal etc. The measuring unit 114 may include a summing-averaging processing part 121 and a noise level detection part 122.

The summing-averaging processing part 121 sequentially sums the VEP signal etc. based on the waveform data from the waveform processing unit 13 at every stimulation until the number of stimulations, having been applied, reaches a predetermined number of times after the start of the measurement of the VEP signal etc. to thereby obtain an average VEP. Then, the VEP signal etc. is sequentially summed at every stimulation until the number of stimulations, having been applied, reaches twice the predetermined number of times after the start of the measurement of the VEP signal etc. to thereby obtain another average VEP. Hereinafter, in the similar manner, an average VEP is obtained each time the number of succeeding stimulations, having been applied, reaches the predetermined number of times after the start of the measurement.

The noise level detection part 122 detects a noise level from the measurement start time point each time the number of stimulations, having been applied, reaches the predetermined number of times. To be explained in detail, the timings for applying stimulations (hereinafter called stimulation timings) in the stimulation unit 119 is inputted into the measuring unit 114. Wave within a time period (hereinafter called a reference time period) determined with reference to the stimulation timing is taken out to thereby obtain a maximum potential difference of the wave (a potential difference between the highest potential and the lowest potential of the wave). Then, an average value of the maximum potential differences within the predetermined number of stimulations is obtained. Thereafter, a standard deviation (SD) of the maximum potential difference is obtained based on differences between the maximum potential differences in the waves at respective stimulations and the average value of the maximum potential differences. The standard deviation thus obtained is set as a noise level at this time point.

The reference time period may be a time period after the stimulation timing. Alternatively, the reference time period may be a time period during which it is expected that the VEP signal is disappeared, that is, a time period just before the next stimulation timing. When the reference time period is set as the latter case, favorably only random noise appears at the time period.

The aforesaid noise level at this time point can also be obtained by using the average VEP which is obtained each time the number of succeeding stimulations having been applied reaches the predetermined number of times. To be concrete, a standard deviation is obtained based on respective potentials of the waves of the average VEP existing within the reference time period and an average value thereof, and this standard deviation is set as the noise level at this time point. Alternatively, a difference between the maximum value and the minimum value of the potential of the waves existing within the reference time period, that is, the maximum potential difference may be set as the noise level at this time point.

The noise levels obtained for the respective predetermined number of succeeding stimulations are displayed on a display part 31 in correspondence to the respective predetermined number of succeeding stimulations by means of a display control part 32. This display differs from that of the first embodiment in a point that the noise levels are displayed in correspondence to the respective predetermined number of succeeding stimulations instead of the respective lapses of the succeeding predetermine time periods. The display control part 32 also displays the average VEPs obtained by the measuring unit 114 in correspondence to the respective predetermined number of succeeding stimulations. The noise levels may be displayed in correspondence to respective integer multiple of the predetermined number of succeeding stimulations.

Like the first embodiment, the noise levels can be predicted by a prediction unit 15. The display control part 32 displays the predicted noise levels on the screen of the display part 31. Concerning a display mode, the predicted noise levels are displayed in the similar manner as the curves EL shown in FIGS. 6 and 7 as explained in the first embodiment.

Since the image is displayed in the aforesaid manner, in a case where large noise levels are continued, for example, a command for stopping the VEP measurement can be inputted from an input unit 18 to thereby stop the operations of the respective units via a control unit 17. Then, after checking the electrodes of the electrode unit 111 etc., a command for starting the VEP measurement can be inputted again from the input unit 18 to thereby perform the VEP measurement. Further, in a case where noise level reduces rapidly, the measurement can be terminated early. Thus, the test can be performed efficiently Further, even in a case where the reduction of noise level can not be expected according to the prediction result, the command for stopping the VEP measurement can be inputted from the input unit 18 to thereby stop the operations of the respective units via the control unit 17. Thus, the measurement can be performed efficiently without continuing for a long time such the measurement large in the noise level and low in the reliability.

According to the biological signal averaging processing device of this presently disclosed subject matter, the detected noise levels are displayed on the screen of the display unit in the chronological manner in association with the respective succeeding predetermined time periods or the respective predetermined number of the succeeding analogous waves. Thus, since the change of the noise levels according to the time lapse can be seen obviously, the state that random noise is removed can be seen in an easily understood manner.

According to the biological signal averaging processing device of this presently disclosed subject matter, when the noise level becomes large during the signal-averaged electrocardiogram test, the measurement can be stopped earlier and then the next measurement can be performed. Thus, since the test time can be shortened as a whole in order to obtain the signal-averaged electrocardiogram at the time where the noise level is smaller than the predetermined level, bearing of a person to be tested can be reduced.

According to the biological signal averaging processing device of this presently disclosed subject matter, the noise levels displayed on the display unit are at least one of the numerical values and the graphs each of which are related to the respective succeeding predetermined time periods or the respective predetermined number of the succeeding analogous waves. Thus, the noise levels can be seen obviously. In this case, since the display mode of noise levels displayed on the screen of the display unit is changed when the noise level exceeds the threshold value, conveniently it becomes possible to predict a time until the termination of the measurement in association with the threshold value. Further, since the display mode is changed by change of color, change of texture, or at least one of change of thickness, size, font and style of characters, the relation with the threshold value can be notified clearly.

According to the biological signal averaging processing device of this presently disclosed subject matter, noise levels after the newest noise-level detection time point are predicted by using noise levels having been detected, and the predicted noise levels are displayed. Thus, it is possible to determine whether the measurement is to be continued or the measurement is to be stopped and performed again. As a result, the test time can be shortened as a whole and bearing of a person to be tested can be reduced. In this case, noise levels having been detected until the newest noise-level detection time point are displayed in association with the respective succeeding predetermined time periods or the respective predetermined number of the succeeding analogous waves, together with the predicted noise levels. Thus, conveniently it is expected that the displayed noise levels are useful for the determination of a medical staff who watches the screen.

What is claimed is:

1. A biological signal averaging processing device comprising:
    a signal acquisition unit configured to continuously obtain a biological signal in which analogous waves appear repeatedly; and
    a summing-averaging processing unit configured to subject the analogous waves obtained by the signal acquisition unit to a summing-averaging processing to thereby obtain an average wave each time succeeding predetermined time period lapses after a desired start time point or each time a predetermined number of succeeding analogous waves appear after the desired start time point, thereby taking out a biological signal from which random noise contained therein is removed, the biological signal averaging processing device further comprising:
    a noise level detection unit configured to detect noise levels of the random noise contained in the biological signal which is obtained by the signal acquisition unit, each time the succeeding predetermined time period lapses after the desired start time point or each time the predetermined number of the succeeding analogous waves appear after the desired start time point;
    a display unit configured to display information; and
    a display control unit configured to display information on a screen of the display unit, wherein
    the display control unit displays the noise levels detected by the noise level detection unit in a chronological manner in association with the respective succeeding predetermined time periods or the respective predetermined number of the succeeding analogous waves,
    the biological signal is an electroencephalographic signal,
    the summing-averaging processing unit subjects the electroencephalographic signal obtained by the signal acquisition unit to the summing-averaging processing to obtain a signal-averaged electrocardiogram, each time the succeeding predetermined time period lapses after the desired start time point, and
    the signal-averaged electrocardiogram, at a time where the noise level of the random noise detected by the noise level detection unit is smaller than a predetermined level, is used for a signal-averaged electrocardiogram test.

2. The biological signal averaging processing device according to claim 1, wherein
    the display control unit displays noise levels on the display unit as at least one of numerical values and graphs each of which are related to the respective succeeding predetermined time periods or the respective predetermined number of the succeeding analogous waves.

3. The biological signal averaging processing device according to claim 1, wherein
    the display control unit changes a display mode of noise levels displayed on the screen of the display unit when the noise level exceeds a threshold value.

4. The biological signal averaging processing device according to claim 3, wherein the display mode is changed by change of color, change of texture, or at least one of change of thickness, size, font and style of characters.

5. A biological signal averaging processing device comprising:
a signal acquisition unit configured to continuously obtain a biological signal in which analogous waves appear repeatedly; and
a summing-averaging processing unit configured to subject the analogous waves obtained by the signal acquisition unit to a summing-averaging processing to thereby obtain an average wave each time succeeding predetermined time period lapses after a desired start time point or each time a predetermined number of succeeding analogous waves appear after the desired start time point, thereby taking out a biological signal from which random noise contained therein is removed, the biological signal averaging processing device further comprising:
a noise level detection unit configured to detect noise levels of the random noise contained in the biological signal which is obtained by the signal acquisition unit, each time the succeeding predetermined time period lapses after the desired start time point or each time the predetermined number of the succeeding analogous waves appear after the desired start time point;
a display unit configured to display information; and
a display control unit configured to display information on a screen of the display unit,
wherein
the display control unit displays the noise levels detected by the noise level detection unit in a chronological manner in association with the respective succeeding predetermined time periods or the respective predetermined number of the succeeding analogous waves,
further comprising:
a noise level prediction unit configured to predict noise levels after a newest noise-level detection time point by using noise levels having been detected by the noise level detection unit, wherein
the display control unit displays noise levels predicted by the noise level prediction unit on the screen of the display unit.

6. The biological signal averaging processing device according to claim 5, wherein
the display control unit displays, on the screen of the display unit, the noise levels having been detected until the newest noise-level detection time point in association with the respective succeeding predetermined time periods or the respective predetermined number of the succeeding analogous waves, together with the predicted noise levels.

* * * * *